(12) United States Patent
Kooijman et al.

(10) Patent No.: US 7,030,270 B2
(45) Date of Patent: Apr. 18, 2006

(54) PROCESS FOR PREPARING MONOCHLOROACETIC ACID

(75) Inventors: Cornelis Kooijman, Deventer (NL); Jacobus Theodorus Jozef Aaldering, Doesburg (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/495,367

(22) PCT Filed: Nov. 19, 2002

(86) PCT No.: PCT/EP02/12944

§ 371 (c)(1), (2), (4) Date: Feb. 14, 2005

(87) PCT Pub. No.: WO03/048098

PCT Pub. Date: Jun. 12, 2003

(65) Prior Publication Data

US 2005/0148794 A1    Jul. 7, 2005

(30) Foreign Application Priority Data

Dec. 4, 2001  (EP) .................................. 01204651

(51) Int. Cl.
*C07C 51/00*  (2006.01)
(52) U.S. Cl. .................................................... 562/603
(58) Field of Classification Search ..................... None
See application file for complete search history.

(56) References Cited

U.S. PATENT DOCUMENTS

| 3,393,235 A | 7/1968 | Boullay |
| 5,756,840 A | 5/1998 | Ebmeyer et al. |

FOREIGN PATENT DOCUMENTS

| GB | 1411214 | * 10/1975 |
| GB | 1 456 057 | 11/1976 |
| JP | A 4-338357 | 11/1992 |
| JP | A 8-231465 | 9/1996 |

* cited by examiner

Primary Examiner—Paul A. Zucker
(74) Attorney, Agent, or Firm—Oliff & Berridge, PLC

(57) ABSTRACT

The invention relates to a process for preparing monochloroacetic acid (MCA) comprising a chlorination step and a hydrogenation step and is characterized in that said process comprises the removal of aldehydes from a process stream by oxidation using a peroxycarboxylic acid. A preferred peroxycarboxylic acid comprises peracetic acid. Preferably, the process is carried out at a temperature of 60–100° C., most preferably at atmospheric pressure. Preferably, an about equimolar amount of peroxycarboxylic acid is used relative to the molar amount of aldehydes present in the process stream. A practical choice for the process stream is the acetic acid recycle stream. The invention process provides a clear and colourless MCA end product.

9 Claims, No Drawings

PROCESS FOR PREPARING MONOCHLOROACETIC ACID

The present invention relates to a new process for preparing monochloroacetic acid (MCA).

A known process for preparing MCA is a two-step process comprising a chlorination step and a hydrogenation step. In the first step, acetic acid is reacted with chlorine in the presence of acetic anhydride, which is converted in situ into the catalyst of this reaction, acetyl chloride. The main reaction products are MCA, hydrogen chloride, and dichloroacetic acid (DCA), which may be present in the reaction product mixture in an amount of up to 6 wt %. In the second step, the reaction product mixture of the first step—containing MCA, DCA, and acetic acid—is subjected to hydrogenation in order to convert DCA into MCA, thereby reducing the amount of DCA in the final product to typically approx. 0.05 wt %.

A disadvantage of this process is that during the hydrogenation step several aldehydes are formed. As a result, the final MCA product may become coloured. Further, the presence of aldehydes in various process streams may cause fouling of some parts of the equipment used for the manufacture of MCA on a technical scale. It also adds to the emission to the environment of the production site.

Hence, there is a need in the art of manufacturing MCA on a technical scale for a solution to these problems.

The present invention offers a solution to the aforementioned problems and provides a clear and colourless MCA end product.

The process for preparing monochloroacetic acid comprising a chlorination step and a hydrogenation step according to the present invention is characterized in that said process comprises the removal of aldehydes from a process stream by oxidation using a peroxycarboxylic acid.

Incidentally, JP-A-04338357 discloses a process for the purification of acetic acid comprising the addition of hydrogen peroxide to acetic acid and distilling the resulting matter. It is mentioned that reducing impurities, especially acetaldehyde, are removed by this process.

Further, JP-A-7326738 discloses a process for producing monochloroacetic acid comprising the oxidation of chloroacetaldehyde with hydrogen peroxide at temperatures almost equal to the reflux temperature of the reaction mixture.

These prior art documents do not, however, relate to a process for preparing MCA comprising a chlorination step and a hydrogenation step. Furthermore, we surprisingly found that hydrogen peroxide does not provide the required selectivity, since its use in the above-described MCA manufacturing process generates chlorine from hydrogen chloride and/or MCA, which in turn leads to the formation of chlorinated aldehydes such as chloroacetaldehyde, dichloroacetaldehyde, and trichloroacetaldehyde—which is undesired. Also, hydrogen peroxide is much slower in oxidizing aldehydes than the peroxycarboxylic acids to be used in accordance with the present invention.

Any peroxycarboxylic acid is suitable for use in accordance with the present invention. Preferably, the peroxycarboxylic acid should be compatible with the above-described manufacturing process for preparing MCA. For example, aqueous solutions of peroxycarboxylic acids are less suitable for use in the invention process. Examples of suitable peroxycarboxylic acids include peracetic acid, perpropionic acid, diperoxydodecanedioic acid, diperoxyisophthalic acid, monoperoxyphthalic acid, decylbutanediperoxycarboxylic acid, 3-chloroperbenzoic acid, and peroxydodecanoic acid.

Preferably, the peroxycarboxylic acid is a $C_1$–$C_{24}$ monoperoxycarboxylic acid. More preferably, the peroxycarboxylic acid is a $C_1$–$C_{12}$ monoperoxycarboxylic acid. Most preferably, the peroxycarboxylic acid comprises peracetic acid. Peracetic acid is commercially available as an equilibrium mixture comprising acetic acid—hydrogen peroxide—peracetic acid—water, with a peracetic acid content of up to 40% by weight.

The amount of peroxycarboxylic acid to be used in the process of the present invention typically is dependent on the amount of aldehydes present in the process stream to be treated. In practice, an about equimolar amount of peroxycarboxylic acid is used relative to the molar amount of aldehydes present. If a molar excess is used, any unreacted peroxycarboxylic acid needs to be destroyed. If less than an equimolar amount is used, the removal of aldehydes from the process streams may not be complete.

The peroxycarboxylic acid to be used in accordance with the present invention is added to the process stream in any conventional way. The reaction conditions should be such that accumulation of the peroxycarboxylic acid is prevented.

The oxidation in accordance with the present invention may be carried out in a wide temperature range, typically from −20° C. to 150° C. A practical temperature range for carrying out the oxidation is 60–100° C. A preferred temperature range is 70–90° C., more preferably it is about 80° C.

The invention process may be carried out in a wide pressure range, either under a vacuum or at pressures up to $10 \times 10^5$ Pa (i.e. 10 bara). Preferably, the process is carried out at pressures up to $6 \times 10^5$ Pa, more preferably up to $3 \times 10^5$ Pa. Most preferably, the process in accordance with the present invention is carried out at atmospheric pressure.

Any process stream of the process for manufacturing MCA on a technical scale which contains aldehydes can be treated in accordance with the present invention. Typically, the reaction product of the hydrogenation step of the manufacturing process described above is subjected to vacuum distillation and the light ends fraction containing acetic acid is recycled to the chlorination unit. The acetic acid recycle process stream is a practical choice for applying the invention process. Other suitable process streams include the hydrogenation product stream and the (absorbed) off-gas of the light ends distillation column.

The present invention is illustrated by the following examples.

EXAMPLES

As an Example, peracetic acid obtained from Fluka (equilibrium mixture containing 39 wt % peracetic acid in acetic acid, 3 wt % hydrogen peroxide, and 14 wt % water) was used. As a Comparative Example, hydrogen peroxide (70 wt % in water) was used.

All experiments were carried out in a batch reactor equipped with a heating jacket, a reflux condenser, and a 4-pitched-blade glass stirrer, at 80° C. and 1 bara (i.e. $1 \times 10^5$ Pa) pressure. Peracetic acid or hydrogen peroxide was dosed to the reactor using a peristaltic pump.

Samples were taken from the acetic acid recycle process stream of a commercial MCA plant having the following typical composition: 80–95 wt % acetic acid, 0–15 wt % MCA, 1–5 wt % water, 0.5–1 wt % hydrogen chloride, and 0.5–1.5 wt % aldehydes. The hydrogen chloride was largely removed by stripping at 60° C./100 mbar (i.e. $1 \times 10^4$ Pa) (final content approx. 70 ppm) before the addition of peracetic acid or hydrogen peroxide was performed.

The presence of acetaldehyde (ACA), chloroacetaldehyde (CAA), dichloroacetaldehyde (DCAA), and crotonaldehyde (CA) was analyzed in intermittently taken samples of the peracetic acid or hydrogen peroxide-treated reaction mixture according to an HPLC method known to a person of ordinary skill in the art.

Example 1

A 2.2-fold molar excess of peracetic acid was dosed in 16 min with a pump to a one-litre stirred batch reactor containing approx. 400 g of an acetic acid recycle sample, heated to 80° C.

After 30 min practically all aldehydes were converted/removed from the reaction mixture. No increase in the amounts of CAA and DCAA was observed.

Example 2

A 5-fold molar excess of peracetic acid was dosed in 16 min with a pump to a one-litre stirred batch reactor containing approx. 400 g of an acetic acid recycle sample, heated to 80° C. In this Example, an acetic acid recycle sample was used where the hydrogen chloride was not removed by stripping.

Again, after only 50 min practically all aldehydes were converted/removed from the reaction mixture and no increase in the amounts of CAA and DCAA was observed.

Comparative Example A

A 4.5-fold molar excess of hydrogen peroxide was dosed in 17 min with a pump to a one-litre stirred batch reactor containing approx. 400 g of an acetic acid recycle sample, heated to 80° C.

A strong increase in the amount of CAA—and to a lesser extent of DCAA—was observed between 4 and 30 min. After 70 min the ACA was nearly completely converted/removed from the reaction mixture, but there still was a considerable amount of CM present—and some DCAA. After 150 min almost all CAA and DCAA was converted.

In conclusion, the removal of aldehydes from a process stream of an MCA manufacturing plant with peracetic acid—a peroxycarboxylic acid in accordance with the present invention—proceeds faster, is more selective, and requires less oxidizing agent than when hydrogen peroxide is used.

An additional advantage is that peroxycarboxylic acids are available as non-aqueous solutions or as formulations containing less water than hydrogen peroxide formulations, which are only available in the form of aqueous solutions. Therefore, less or no water at all is introduced in the process of preparing monochloroacetic acid, which is an anhydrous process.

The invention claimed is:

1. A process for preparing monochloroacetic acid comprising a chlorination step and a hydrogenation step, said process comprising the removal of aldehydes from a process stream by oxidation using a peroxycarboxylic acid.

2. A process according to claim 1, characterized in that the peroxycarboxylic acid is a $C_1$–$C_{24}$ monoperoxycarboxylic acid.

3. A process according to claim 1, characterized in that the peroxycarboxylic acid comprises peracetic acid.

4. A process according to claim 1, characterized in that the peroxycarboxylic acid is used in an about equimolar amount relative to the molar amount of the aldehydes present in the process stream.

5. A process according to claim 1, characterized in that the oxidation is carried out at a temperature of 60–100° C.

6. A process according to claim 1, characterized in that the oxidation is carried out at a temperature of 70–90° C.

7. A process according to claim 1, characterized in that the oxidation is carried out at pressures up to $6 \times 10^5$ Pa.

8. A process according to claim 1, characterized in that the oxidation is carried out at atmospheric pressure.

9. A process according to claim 1, characterized in that the process stream is the acetic acid recycle stream.

\* \* \* \* \*

UNITED STATES PATENT AND TRADEMARK OFFICE
CERTIFICATE OF CORRECTION

PATENT NO. : 7,030,270 B2  
APPLICATION NO. : 10/495367  
DATED : April 18, 2006  
INVENTOR(S) : Cornelis Kooijman and Jacobus Theodorus Jozef Aaldering It is certified that error appears in the above-identified patent and that said Letters Patent is hereby corrected as shown below:

Column 3, line 40, change "CM" to --CAA--.

Signed and Sealed this

Eighteenth Day of July, 2006

JON W. DUDAS  
*Director of the United States Patent and Trademark Office*